(12) United States Patent
Portes et al.

(10) Patent No.: US 10,758,749 B2
(45) Date of Patent: Sep. 1, 2020

(54) COSMETIC OR DERMATOLOGICAL COMPOSITION AND USE THEREOF

(71) Applicant: LABORATOIRES M&L, Manosque (FR)

(72) Inventors: Pascal Portes, Puyricard (FR); Valérie Cenizo, Meyrargues (FR); Géraldine Lemaire, Valensole (FR)

(73) Assignee: LABORATORIES M&L, Manosque (FR)

( * ) Notice: Subject to any disclaimer, the term of this patent is extended or adjusted under 35 U.S.C. 154(b) by 260 days.

(21) Appl. No.: 15/774,183

(22) PCT Filed: Nov. 2, 2016

(86) PCT No.: PCT/FR2016/052835
§ 371 (c)(1),
(2) Date: May 7, 2018

(87) PCT Pub. No.: WO2017/077232
PCT Pub. Date: May 11, 2017

(65) Prior Publication Data
US 2018/0318205 A1    Nov. 8, 2018

(30) Foreign Application Priority Data
Nov. 6, 2015 (FR) ..................................... 15 60663

(51) Int. Cl.
| *A61Q 19/08* | (2006.01) |
| *A61Q 17/00* | (2006.01) |
| *A61K 8/9717* | (2017.01) |
| *A61K 8/9789* | (2017.01) |

(52) U.S. Cl.
CPC ............ *A61Q 19/08* (2013.01); *A61K 8/9717* (2017.08); *A61K 8/9789* (2017.08); *A61Q 17/00* (2013.01)

(58) Field of Classification Search
CPC ...... A61K 8/97; A61K 8/9717; A61K 8/9789; A61K 2300/00; A61K 36/28; A61K 36/53; A61K 2800/591; A61K 47/44; A61K 8/062; A61K 8/064; A61K 8/922; A61K 8/9783; A61K 9/0014; A61K 9/107; A61Q 17/00; A61Q 19/08; A61Q 19/00; A61Q 19/007; A61P 25/02
See application file for complete search history.

(56) References Cited

U.S. PATENT DOCUMENTS

2009/0269419 A1    10/2009 Pierrisnard et al.

FOREIGN PATENT DOCUMENTS

| FR | 2829145 A1 | 3/2003 |
| FR | 3000389 A1 | 7/2014 |

OTHER PUBLICATIONS

Database GNPD [Online] MINTEL; Jun. 2015, Delaron: "Slimming Perfection Cream," XP002757729, Database accession No. 3079483.
"Ultimate Youth Serum," GNPD; MINTEL, Sep. 2011, XP002718573.
"Lifting Radiance Serum," GNPD; MINTEL, Oct. 2010, XP002715058.
Sala, A., et al., "Anti-Inflammatory and Antioxidant Properties of Helichrysum Italicum," J. Pharmacy and Pharmacology 2002;54(3):365-371, XP008025203.
International Search Report for PCT Patent App. No. PCT/FR2016/052835 (dated Feb. 1, 2017) with English translation.

*Primary Examiner* — Aaron J Kosar
(74) *Attorney, Agent, or Firm* — Kenealy Vaidya LLP

(57) ABSTRACT

Some embodiments are directed to a cosmetic composition including at least one extract of *Jania rubens* and at least one extract of everlasting. Some embodiments are also directed to the cosmetic use of a composition including at least one extract of *Jania rubens* and at least one extract of everlasting. Some embodiments are also directed to a non-therapeutic anti-ageing cosmetic treatment and/or the protection of the skin against external attacks, using a cosmetic composition including at least one extract of *Jania rubens* and at least one extract of everlasting. Some embodiments particularly apply to the cosmetic and/or dermatological fields.

15 Claims, No Drawings

COSMETIC OR DERMATOLOGICAL COMPOSITION AND USE THEREOF

CROSS REFERENCE TO RELATED APPLICATIONS

This application is a national phase filing under 35 C.F.R. § 371 of and claims priority to PCT Patent Application No. PCT/FR2016/052835, filed on Nov. 2, 2016, which claims the priority benefit under 35 U.S.C. § 119 of French Patent Application No. 1560663, filed on Nov. 6, 2015, the contents of each of which are hereby incorporated in their entireties by reference.

BACKGROUND

Some embodiments relate to a cosmetic composition containing an extract of slender-beaded coral weed and at least one extract of everlasting.

Some embodiments also relate to the cosmetic use of a composition including an extract of slender-beaded coral weed and at least one extract of everlasting. In particular, some embodiments relate to the nontherapeutic cosmetic use of a composition including an extract of slender-beaded coral weed and at least one extract in a nontherapeutic antiaging cosmetic treatment.

Some embodiments also relate to the cosmetic use of a composition including an extract of slender-beaded coral weed and at least one extract of everlasting in a nontherapeutic cosmetic treatment for protecting the skin against external attack.

Some embodiments also relate to a nontherapeutic cosmetic treatment process including the application of a cosmetic composition including an extract of slender-beaded coral weed and at least one extract of everlasting.

Some embodiments also relate to a cosmetic care kit especially including a cosmetic composition including an extract of slender-beaded coral weed and at least one extract of everlasting.

Some embodiments provide an application especially in the cosmetic and/or dermatological fields.

In the description below, the references in square brackets ([ ]) refer to the list of references presented at the end of the text.

The skin has a very complex architecture. As a barrier between the external environment and the internal medium of our body, its functioning serves two purposes: ensuring communication between the organism and the external environment, and protecting it against attack [1].

With age, the various cutaneous structures are modified both morphologically and functionally. The main consequences are a decline in the defense, cicatrization, perception and thermoregulation functions and also the establishment of a chronic inflammatory state corresponding to an increase in the number of macrophages and persistent cutaneous dryness [2].

In the epidermis, its turnover passes from 21 days to 40 days, which accounts for the negative impact on cicatrization and tissue repair [3]. The keratinocytes become smaller and fewer in number. The cell turnover slows down and the cohesion between the dermis and the epidermis becomes attenuated.

By its constant turnover, the epidermis is the physical barrier against chemical, physical and bacterial attack. The epidermal keratinocytes undergo morphological and biochemical changes when they migrate from the basal layer to the spinous and granulous layers to form the stratum corneum. Various proteins characterize each layer of the epidermis: keratins 5 and 14 are the main keratins of the basal layer, whereas keratins 1, 2 and 10 are expressed by the suprabasal keratinocytes. Certain proteins that are associated with differentiation, such as involucrin, loricrin and filaggrin, are expressed solely in the differentiated layers of the epidermis [4, 5, 6].

The cornification process is initiated in the stratum spinosum with the expression of the proteins involucrin [7], periplakin [8] and envoplakin [9]. Initially, these two members of the plakin family (periplakin and envoplakin) form a complex with involucrin and are attached to the inner surface of the plasma membrane [10], forming an assembly [11]. The recruitment and binding of periplakin and envoplakin to the lipid bilayer may require the presence of calcium. These three proteins (envoplakin, involucrin and periplakin) are crosslinked by transglutaminase 1, the enzymatic activity of which is calcium-dependent. Continuous formation of the cornified envelope may require the production of lamellar bodies in the stratum granulosum. Secretion of the content of the lamellar bodies gives the skin its impermeability and protects it against bacteria.

The main component of the cornified envelope is loricrin. This protein represents more than 80% of the mass of proteins of the cornified envelope and is expressed in the stratum granulosum [12]. The synthesis of loricrin may require a calcium concentration of about 0.1 mM. During the process of formation of the cornified envelope, loricrin is crosslinked with itself and with the members of the SPRR (small proline rich repeat) family [13, 14]. The addition of calcium to keratinocytes in primary culture greatly increases the expression of SPRRs. They are thus crosslinked with loricrin via the Nε-(γ-glutamyl)lysine (isopeptide) bridges by transglutaminases 1 and 3 [13, 15]. During the final process of formation of the cornified envelope, the loricrin-SPRR assembly is transported to the cell membrane and attached to the periplakin-involucrin-evoplakin assembly [12]. The final proteins incorporated in the cornified envelope are the members of the "late cornified envelope" (LCE) family [16, 17].

Within the epidermis, the keratinocytes have different calcium needs. The keratinocytes of the basal layer may require very low calcium concentrations allowing the division of stem cells which ensure the epidermal renewal. Whereas high calcium concentrations may be required for the differentiation program resulting in the formation of corneocytes and of the cornified envelope. In order for the keratinocytes to encounter these various concentrations, a calcium gradient is constructed within the epidermis. In elderly people, the calcium gradient is greatly perturbed. Specifically, in young people or young adults, a calcium peak is clearly observed in the upper layer of the stratum granulosum, whereas, in elderly people, calcium is distributed homogeneously in all the layers of the epidermis [18].

Filaggrin is produced by the granulous keratinocytes in the form of a precursor known as profilaggrin, which includes 10-12 filaggrin units. It is the major component of keratohyalin granules. During the transition of the granules to the cornified envelope, profilaggrin is rapidly dephosphorylated and cleaved by certain proteases such as caspase-14, bleomycin hydrolase and calpain 1 [19, 20, 21] to generate filaggrin monomers [21]. These filaggrin monomers associate with keratin filaments and are suspected to induce the formation of the fibrous matrix of the corneocytes [22]. In the cornified cells, filaggrin is degraded into free amino acids and other components of the natural skin moisturizing factor. These free amino acids may be necessary for photoprotection of the skin (urocanic acid) and also the acidification and moisturization (pyrrolidonecarboxylic acid) of the stratum corneum [21, 23, 24].

With age, the turnover of the keratinocytes is considerably reduced and the protein composition of the cornified envelope responsible for the barrier function is profoundly modified. It is thus of importance to restore the keratinocyte proliferation and also their differentiation potential for the purpose of restoring the epidermal homeostasis and the barrier function of the skin which are perturbed by aging of the skin.

Moreover, with age, the skin loses its firmness and its elasticity, which may especially be the cause of the appearance of wrinkles both on the face and over the entire body.

SUMMARY

Many cosmetic compositions for treating aging of the skin and/or for firming the skin exist in the related art. However, these compositions have relative efficacies, or their efficacies are even contested in certain cases by consumer associations. The relative efficacy of the related art compositions may be at the root of a need for individuals to resort to surgical acts such as the injection of hyaluronic acid and/or botulinum toxin in order to conceal wrinkles.

An aqueous or aqueous-glycerol extract of *Jania rubens* is known as being able to stimulate the synthesis of collagen fibers, to inhibit the differentiation of adipocytes and to stimulate lipolysis (patent FR3000389) [25]. Essential oil of everlasting is also known to have free-radical-scavenging properties, to stimulate the synthesis of collagen fibers and to stimulate the expression of sirtuin 1 and/or to induce the gene expression of loricrin and two "S100 calcium binding proteins" (S100A7 and S100A9) which are proteins involved in epidermal differentiation [26, 27, 28, 29].

However, these compositions do not in principle make it possible to efficiently treat both intrinsic and extrinsic aging of the skin, the causes of this aging of the skin, while at the same time protecting the skin against external attack. In other words, the related art cosmetic compositions have relative effects for which there is a real need for compositions and/or methods for treating intrinsic and extrinsic aging of the skin, the causes of this aging of the skin, while at the same time protecting the skin against external attack.

Many cosmetic compositions for treating aging of the skin and/or for firming the skin also exist in the related art. However, these compositions, like those mentioned above, have relative efficacies.

There is thus a real need to find antiaging cosmetic compositions that can especially reinforce the cutaneous barrier, smooth out the surface of the skin, firm the skin and/or prevent or treat aging of the skin, for example intrinsic and/or extrinsic aging of the skin.

Some embodiments address these needs and drawbacks by providing a cosmetic composition including at least one extract of slender-beaded coral weed and at least one extract of everlasting.

The inventors of some embodiments are, in point of fact, the very first to have demonstrated, entirely unexpectedly, that a cosmetic composition including both at least one extract of slender-beaded coral weed and at least one extract of everlasting advantageously allows an antiaging effect, especially by stimulating the proliferation and differentiation of epidermal cells, while at the same time protecting against external attack by reinforcing the skin's barrier function.

In addition, the inventors of some embodiments also demonstrated, surprisingly and unexpectedly, that a cosmetic composition including both at least one extract of slender-beaded coral weed and at least one extract of everlasting advantageously makes it possible to maintain the moisturization of the skin while at the same time stimulating epidermal turnover.

In the present text, the term "extract" means any form of extract known to those of ordinary skill in the art. It may be, for example, a liposoluble extract, a water-soluble extract, an oily extract, an aqueous extract, an aqueous-alcoholic extract, an aqueous-glycerol extract, a supercritical extract, an essential oil or any mixture thereof.

In the present text, the extract may be obtained, for example, from all or part of a plant. It may be, for example, an extract obtained from flowers or floral heads, leaves, seeds, roots, stems or pericarp. It may be, for example, an extract obtained from whole flowers.

In the present text, the term "liposoluble extract" means an extract rich in fatty acid and/or in fat and/or a water-insoluble extract. According to some embodiments, the oily extract may be any oily extract obtained via any process known to those of ordinary skill in the art. For example, it may be obtained by extraction assisted by high frequencies or by ultrasound, by supercritical extraction, or by maceration in an oily solvent [30].

In the present text, the term "water-soluble extract" means an extract that is soluble in water. It may be an aqueous, aqueous-alcoholic, aqueous-glycerol extract; obtained by distillation, by maceration, by assisted extraction, by subcritical extraction, by high frequencies or by ultrasound [30].

In the present text, the term "everlasting" means a species of floral plants of the Asteraceae family and of the genus *Helichrysum*. In particular, it may be *Helichrysum italicum*, which may be present throughout the Mediterranean. It may be, for example, the everlasting described in French patents FR0111224, FR0605953 and FR0905904 [26, 27, 28].

According to some embodiments, the "extract of everlasting" may be a liposoluble extract, a water-soluble extract, an essential oil or a mixture thereof.

According to some embodiments, the extract of everlasting may be chosen from the group including an aqueous extract of everlasting, an oily extract of everlasting, an essential oil of everlasting or a mixture thereof. In the present text, the liposoluble extract may be obtained from a plant and/or from a plant part. It may be, for example, an oily extract obtained from flowers or floral heads, leaves, seeds, roots, stems or pericarps.

It may be, for example, a liposoluble extract of everlasting obtained via any process known to those of ordinary skill in the art. It may be, for example, an oily extract rich in fatty acid and/or in fat obtained via any process known to those of ordinary skill in the art. For example, it may be an oily extract obtained by oily extraction with microwaves, by high frequency, by supercritical extraction, by maceration in an oily solvent, or by ultrasound-assisted oily extraction. It may be, for example, a biological oily extract of everlasting by ultrasound-assisted microwave extraction according to a process including a first step of grinding the floral heads of everlasting followed by ultrasound- and microwave-assisted extraction, and then clarification and finally a filtration step in order to recover the oily extract.

In the present text, the liposoluble extract may be an oily extract, an essential oil and/or a supercritical $CO_2$ extract.

In the present text, the essential oil may be obtained, for example, from an oil obtained from flowers or floral heads, leaves, seeds, roots or stems. It may be, for example, an essential oil of everlasting obtained from floral heads. It may be, for example, a biological essential oil of everlasting, i.e. derived from biological agriculture, for example a biological essential oil from Corsica, for example from the companies TEPPE ROSSE, STEPHAN FRANCISCI, GAEC de l'ASTRATELLA or a mixture of two or three of these oils.

In the present text, the biological essential oil of everlasting may include from 25% to 50% by weight of neryl acetate and/or from 2% to 15% of italidiones. For example, the biological essential oil of everlasting may include from 25% to 50% by weight of neryl acetate and/or from 2% to 10% of italidiones.

In the present text, the oily extract of everlasting may include from 0.1% to 0.3% by weight of sugars, for example 0.2% of sugars, from 0.04% to 0.06% by weight of vitamin E, for example 0.051% of vitamin E, from 99% to 99.9% by weight of fatty acids, for example 99.8% by weight of fatty acids, including from 80% to 85% of oleic acid, for example 83.4% of oleic acid, from 6% to 8% of linoleic (omega-6) acid, for example 7.3% of linoleic (omega-6) acid, from 2% to 5% of palmitic acid and from 2% to 4% of stearic acid, but is above all distinguished by its phytosterol content of 0.2% to 0.5%, for example 0.35%, including a majority of beta-sitosterol 0.2% and of polyphenols from 0.01% to 0.1%, for example 0.074%.

In the present text, the supercritical $CO_2$ extract may be obtained, for example, from flowers or floral heads, leaves, seeds, roots or stems. It may be, for example, a supercritical $CO_2$ extract obtained from dry aerial parts or dry floral heads. It may be, for example, an extract obtained from dry aerial parts by performing the extraction process with supercritical fluids, for example supercritical $CO_2$ [31].

In the present text, the water-soluble extract of everlasting may be, for example, a water-soluble extract of everlasting obtained via any process known to those of ordinary skill in the art. It may be, for example, an aqueous extract obtained according to the process described in the publication "Eco-extraction du végétal [Eco-extraction of plants]" [30]. It may be, for example, an "eco-process" extraction process, i.e. a process which consumes less energy than conventional processes. It may be, for example, an ultrasound-assisted extraction process. It may be, for example, a subcritical-water extraction process obtained according to the process described in the publication "Eco-extraction du végétal" [30]. It may be, for example, a biological aqueous extract of everlasting, for example a biological extract of Corsican everlasting from the company Greentech.

In the present text, the aqueous extract may be obtained, for example, from a plant and/or a plant part. It may be, for example, an aqueous extract obtained from flowers or flower heads, leaves, seeds, roots or stems. It may be, for example, an extract obtained from whole flowers.

According to some embodiments, the extract of everlasting may be present in the composition, for example, at a concentration of from 0.01% to 10% by weight relative to the total weight of the composition, for example from 0.01% to 5% by weight relative to the total weight of the composition.

According to some embodiments, the water-soluble extract of everlasting may be present in the composition, for example, at a concentration of from 0.01% to 10% by weight relative to the total weight of the composition, for example from 0.01% to 5% by weight relative to the total weight of the composition.

According to some embodiments, the liposoluble extract of everlasting may be present in the composition, for example, at a concentration of from 0.001% to 10%, from 0.001% to 5% by weight relative to the total weight of the composition, for example from 0.001% to 2% by weight relative to the total weight of the composition.

According to some embodiments, the essential oil of everlasting may be present in the composition from 0.001% to 10%, from 0.001% to 5% by weight relative to the total weight of the composition, for example from 0.001% to 0.5% by weight relative to the total weight of the composition.

According to some embodiments, when the composition includes a liposoluble extract of everlasting, a water-soluble extract of everlasting and essential oil of everlasting, the sum of the liposoluble extract of everlasting, water-soluble extract of everlasting and essential oil of everlasting in the composition of some embodiments may be from 0.001% to 10% by weight relative to the total weight of the composition, for example from 0.001% to 5% by weight relative to the total weight of the composition.

In the present text, the term "slender-beaded coral weed" means an alga belonging to the Corallinaceae family, for example found in the North-East Atlantic, the Mediterranean, the Black Sea, the Indian ocean and the Sea of China. It may be the alga *Jania rubens*, which is a red alga (Rhodophyceae) belonging to the corallinaceae. This alga is a calcified species, consisting of clusters standing on a common basal crust, and may measure about 2 to 3 cm in height. During its slow growth, *Jania rubens* is capable of binding minerals and trace elements from seawater, but also retains marine microflora and micro fauna.

In the present text, the term "extract of slender-beaded coral weed" means an extract of all or part of slender-beaded coral weed. It may be, for example, an extract of wild slender-beaded coral weed and/or of cultivated slender-beaded coral weed.

In the present text, slender-beaded coral weed may be the alga *Jania rubens*.

In the present text, the extract of slender-beaded coral weed may be a water-soluble extract or a liposoluble extract or a mixture thereof.

In the present text, the liposoluble extract of slender-beaded coral weed may be obtained from a plant and/or from a plant part.

In the present text, the liposoluble extract of slender-beaded coral weed may be an oily extract, a supercritical $CO_2$ extract or a mixture thereof.

In the present text, the liposoluble extract of slender-beaded coral weed may be, for example, an oily extract of slender-beaded coral weed obtained via any process known to those of ordinary skill in the art. For example, it may be obtained by high-frequency-assisted or ultrasound-assisted extraction, by supercritical extraction, by maceration in an oily solvent according to the process described in publication [30].

The liposoluble extract of slender-beaded coral weed may be, for example, an oily extract rich in fatty acid and/or fat obtained via any process known to those of ordinary skill in the art. For example, it may be an oily extract obtained by microwave or high-frequency oily extraction, by supercritical extraction, by maceration in an oily solvent, by ultrasound-assisted oily extraction. It may be, for example, a biological oily extract of slender-beaded coral weed by ultrasound-assisted microwave extraction according to a process including a first step of grinding followed by ultrasound-assisted and microwave-assisted extraction, and then clarification and finally a filtration step in order to recover the oily extract.

In the present text, the extract of slender-beaded coral weed may be, for example, a water-soluble extract of slender-beaded coral weed obtained via any process known to those of ordinary skill in the art. It may be, for example, an aqueous extract of slender-beaded coral weed obtained according to the process described in the publication "Eco-extraction du végétal" [30]. It may be, for example, an "eco-process" extraction process, i.e. a process which consumes less energy than related art processes. It may be, for example, an ultrasound-assisted extraction process. It may be, for example, a subcritical-water extraction process as described in the publication "Eco-extraction du végétal" [30]. It may be, for example, an aqueous-alcoholic extraction process. It may be, for example, an aqueous-glycerol extraction process.

In the present text, the water-soluble extract of slender-beaded coral weed may be, for example, an aqueous extract of slender-beaded coral weed obtained via any process known to those of ordinary skill in the art. It may be, for example, an aqueous extract of slender-beaded coral weed that is commercially available; for example, it may be an aqueous extract sold by the company CODIF.

In the present text, the extract of slender-beaded coral weed may be, for example, a water-glycerol extract (50/50 v/v) of slender-beaded coral weed. It may be, for example, a water-glycerol extract of *Jania rubens*, for example a water-glycerol extract that is commercially available, for example sold by the company CODIF under the commercial reference Actiporine 8G.

According to some embodiments, the extract of slender-beaded coral weed may be present in the composition, for example, at a concentration of from 0.001% to 10% by weight relative to the total weight of the composition, for example from 0.001% to 5% by weight relative to the total weight of the composition.

According to some embodiments, the water-soluble extract of slender-beaded coral weed may be present in the composition, for example, at a concentration of from 0.01% to 10% by weight relative to the total weight of the composition, for example from 0.01% to 5% by weight relative to the total weight of the composition.

According to some embodiments, the water-glycerol extract of slender-beaded coral weed may be present in the composition, for example, at a concentration of from 0.01% to 10% by weight relative to the total weight of the composition, for example from 0.01% to 5% by weight relative to the total weight of the composition.

According to some embodiments, the liposoluble extract of slender-beaded coral weed may be present in the composition, for example, at a concentration of from 0.001% to 10% by weight relative to the total weight of the composition, for example from 0.001% to 5% by weight relative to the total weight of the composition.

According to some embodiments, when the composition includes a water-soluble extract of slender-beaded coral weed and a liposoluble extract of slender-beaded coral weed, the sum of the concentrations of the water-soluble extract of slender-beaded coral weed and liposoluble extract of slender-beaded coral weed may be from 0.001% to 10% by weight relative to the total weight of the composition, for example from 0.001% to 5% by weight relative to the total weight of the composition.

Advantageously, the composition according to some embodiments includes at least one water-glycerol extract of slender-beaded coral weed and at least one essential oil of everlasting.

Advantageously, the inventors have demonstrated that a composition including at least one extract of slender-beaded coral weed, for example a water-glycerol extract of slender-beaded coral weed, and at least one extract of everlasting, for example essential oil of everlasting, makes it possible to stimulate epidermal differentiation and to reinforce the barrier function of the skin. In addition, the composition of some embodiments advantageously makes it possible to promote cohesion between the dermis and the epidermis, to regenerate and restructure the epidermis for better surface smoothness and a radiant complexion.

According to some embodiments, irrespective of the extract or mixture of extracts used, the cosmetic composition of some embodiments may also include at least one additional active agent chosen, for example, from an antiaging agent, a moisturizing agent, a lightening agent, a calmative agent, an agent acting on the microcirculation, one or more antioxidant agents, a firming agent, a tensioning agent or a mixture of these agents. These agents may be those commonly used in cosmetic products. Examples of antiaging agents that may be used are, for example, silicon or vitamin C. Examples of moisturizing agents that may be used are, for example, glycerol or hyaluronic acid. Examples of lightening agents that may be used are, for example, arbutin or vitamin C. Examples of calmative agents that may be used are, for example, bisabolol or allantoin. Examples of agents acting on the microcirculation that may be used are, for example, escin or hesperetin from orange. Examples of antioxidant agents that may be used are, for example, Pycnogenol (registered trademark), vitamin C, polyphenols. Examples of firming agents that may be used are, for example, rye derivatives. Examples of tensioning agents that may be used are, for example, exopolysaccharides. This or these agents may be used in the composition of some embodiments, for example, at the concentrations usually used and known to those of ordinary skill in the art in cosmetic or dermatological compositions.

The cosmetic composition according to some embodiments may also include at least one additional active agent chosen, for example, from a conditioning agent and a repairing agent. These agents may be those commonly used in cosmetic and/or dermatological products. Examples of conditioning agents that may be used may be, for example, polysaccharides or hydrolyzed proteins. Repairing agents may be, for example, sunflower, evening primrose or shea butter plant oils.

The cosmetic composition according to some embodiments may include one or more adjuvants known to those of ordinary skill in the art. They may be, for example, one or more adjuvants chosen from agents such as esters, moisturizing agents, emollient agents, emulsifiers, surfactants, mineral thickening agents, organic thickening agents, which may or may not be associative, water-soluble and liposoluble organic sunscreens, mineral sunscreens, silicone compounds, fragrances, preserving agents, ceramides and pseudoceramides, vitamins and provitamins, proteins, sequestering agents, basifying agents, acidifying agents, reducing agents, oxidizing agents, mineral fillers, dyes or any other adjuvants that may be mentioned in the INCI (International Nomenclature of Cosmetic Ingredients) dictionary published by the PCPC (Personal Care Products Council).

According to some embodiments, the cosmetic or dermatological composition may be, for example, in any form known to those of ordinary skill in the art which may be used in the cosmetic field, without any particular presentation restriction. The composition may be in any presentation form known to those of ordinary skill in the art. It may be, for example, an oil-in-water or water-in-oil emulsion, a multiple emulsion, a microemulsion, a nanoemulsion, a solid emulsion, an aqueous or aqueous-alcoholic gel, a mist, an ointment, a mask, a shampoo, a hair conditioner, a serum, a hair lotion, an ointment, a cream, an oil, a milk, a salve, a stick, an impregnated pad, a transdermal patch, a solution, a gel, a spray, a lotion or a suspension, a wax, a two-phase serum, for example including an oily fraction and an aqueous fraction.

According to some embodiments, the cosmetic or dermatological composition may be a topical composition. It may be any topical composition known to those of ordinary skill in the art. It may be, for example, a cream, a serum, a milk, a gel, a lotion, an ointment, a salve, an oil, a balm or a mask.

In the present text, the cosmetic composition may be obtained via any suitable process known to those of ordinary skill in the art for the manufacture of a cosmetic composition. It may be a mixture of surfactant materials in water. It may also be, for example, a process including a step of incorporating an internal phase into an external phase by an emulsifier, for example a turbomixer of rotor-stator type. It may also be, for example, a process using the Phase Inversion Temperature (PIT) process conventionally used by those of ordinary skill in the art to obtain oil-in-water emulsions in which the dispersed droplets are particularly fine, for example with a diameter of from 0.1 to 1 µm.

The inventors have demonstrated, surprisingly and unexpectedly, that the composition including an extract of slender-beaded coral weed and an extract of everlasting advantageously makes it possible, especially by increasing the differentiation of the epidermal cells, to reinforce the barrier function of the skin, to maintain better moisturization, to stimulate the skin's defenses and to enhance or improve the surface quality of the skin.

Also, according to some embodiments, the composition may also be a composition used in a nontherapeutic antiaging cosmetic treatment.

The inventors have also demonstrated, surprisingly and unexpectedly, that the composition including an extract of slender-beaded coral weed and an extract of everlasting advantageously makes it possible to maintain/increase the moisturization of the skin, to prevent and/or treat aging of the skin, for example by conserving and/or restoring the thickness of the epidermis and/or by enhancing or improving the surface quality of the skin.

The inventors have also demonstrated, surprisingly and unexpectedly, that the composition including an extract of slender-beaded coral weed and an extract of everlasting advantageously makes it possible to reduce the density of pigmentation marks caused by aging of the skin and to enhance or improve the uniformity and clarity of the complexion.

According to some embodiments, the composition may also be a composition used in a nontherapeutic antiaging cosmetic treatment, for example in a treatment of aging of the skin, for example wrinkles and fine lines, loss of firmness, loss of elasticity and dry skin.

According to some embodiments, the composition may be a composition used in a nontherapeutic antiaging cosmetic treatment, for example in the treatment of aging of the skin, for example wrinkles and fine lines, loss of firmness, loss of radiance, loss of elasticity and dry skin.

The inventors have also demonstrated, surprisingly and unexpectedly, that the composition including an extract of slender-beaded coral weed and an extract of everlasting advantageously makes it possible to protect the skin against external attack.

In the present text, the term "external attack" means, for example, physical attack, for example by the cold, microorganisms, dust, sunlight and/or ultraviolet (UV), pollution, or chemical attack, for example tobacco, vehicle exhaust gases, fine particles.

Also, a subject of some embodiments is also the use of the composition including at least one extract of slender-beaded coral weed and at least one extract of everlasting in a nontherapeutic cosmetic treatment for protecting the skin against external attack.

In this application, the extract of slender-beaded coral weed is as defined above.

In this application, the extract of everlasting is as defined above.

In this application, the composition is as defined above.

A subject of some embodiments is also a nontherapeutic cosmetic treatment process including the application to the skin of a cosmetic composition including at least one extract of slender-beaded coral weed and at least one extract of everlasting.

The extract of slender-beaded coral weed is as defined above.

The extract of everlasting is as defined above.

The cosmetic composition is as defined above.

For this application, use may be made, for example, of the presentation forms described above. Application to the skin may thus be performed as a function of the presentation form used.

It may be, for example, simple application to the skin or application accompanied by massaging of the skin with the composition of some embodiments.

The application is advantageously or preferably performed with a sufficient amount of the composition so that the entire surface of the skin to be treated is treated. It may be, for example, a standard application, such as a cream on the skin.

It may also be, for example, an application to form a treating mask.

The application may be, for example, a daily, weekly or twice-monthly application. It may be, for example, an application once a day, twice a day or more.

A subject of some embodiments is also a cosmetic care kit including a cosmetic composition according to some embodiments and a support including instructions for the use of the composition.

The support including instructions for the use of the composition may be a manual or a notice for use, especially to explain to the user the manner and frequency of application to the skin of the composition of some embodiments.

According to some embodiments, the cosmetic care kit may also include an applicator, for example a spatula, a brush, a dynamic applicator, for example a massaging device impregnated with the cosmetic composition of some embodiments.

DETAILED DESCRIPTION OF EXEMPLARY EMBODIMENTS

Other characteristics and advantages will also become apparent to a person of ordinary skill in the art on reading the examples below, which are given as nonlimiting illustrations.

EXAMPLES

Example 1: Example of a Facial Care Composition (Cream)

A base composition was prepared according to the following process: the various ingredients were prepared beforehand and weighed out, glycerol was introduced into the water and mixed at 1500 rpm and heated to 80° C., the gelling agent was dispersed in this mixture with stirring at 1500 rpm until dissolved. The oily phase prepared beforehand by mixing, for example, the emulsifying agent, the hard fatty substances, the caprylic capric triglycerides, the ester and the plant oils, with heating, at 80° C., until a homogeneous mixture was obtained, was introduced with stirring at a speed of 1500 rpm until a cream was obtained, which was then cooled to 40° C. with stirring at 1500 rpm. The active agents, for example the trace elements, the vitamin C derivative, and also the fragrance, the preserving agents and the pH regulator, were then added.

Table 1 below summarizes the composition of the cream.

TABLE 1 base composition for the face (cream)

| Ingredients | Amount as weight % relative to the total weight of the composition |
|---|---|
| Emulsifying agent | 1 to 10% |
| Moisturizing agents (glycerol) | 1 to 15% |
| Hard fatty substances | 1 to 5% |
| Caprylic capric triglycerides | 5 to 25% |
| Ester | 10-20% |
| Plant oils | 1-5% |
| Gelling agent | 1-5% |
| Fragrance | QSP |
| Water | QSP |
| Preserving agents | QSP |

Starting with this base composition, for facial care, various compositions in accordance with some embodiments were manufactured by adding an extract of slender-beaded coral weed and an extract of everlasting in various amounts.

The extract of slender-beaded coral weed was a water-glycerol extract (50/50 v/v) of *Janis rubens* sold by the company CODIF under the commercial reference Actiporine 8G.

The extract of everlasting was an essential oil of everlasting obtained by hydrodistillation and provided by the companies TEPPE ROSSE, STEPHAN FRANCISCI, GAEC de l'ASTRATELLA or a mixture of two or three of these oils.

The extract of everlasting was a biological aqueous extract of Corsican everlasting obtained by extraction and provided by the company Greentech.

The extract of everlasting was an oily extract obtained by ultrasound-assisted microwave oily extraction and provided by the company Oléos.

The various ingredients were dispersed using a laboratory mixer such as a bench stirrer.

Starting with the base composition, compositions were prepared including:

- 0.1; 0.05; 0.03; 0.02; 0.01% by weight of oily extract of everlasting relative to the total weight of each composition
- 0.5; 0.2; 0.1; 0.05; 0.02; 0.01% by weight of aqueous extract of everlasting relative to the total weight of each composition
- 0.2; 0.1; 0.05; 0.02; 0.01% by weight of essential oil of everlasting relative to the total weight of each composition
- 3; 2; 1; 0.5; 0.1% by weight of slender-beaded coral weed relative to the total weight of each composition.

The values of fragrance, preserving agent and water then being adjusted as indicated in table 1 above.

The weight percentages of extracts of everlasting and extract of slender-beaded coral weed are indicated in table 2 below.

TABLE 2 weight percentage of oily extract of everlasting, of aqueous extract of everlasting, of essential oil of everlasting and of extract of slender-beaded coral weed relative to the total weight of the composition

| Composition | Weight % of oily extract of everlasting relative to the weight of the composition (%) | Weight % of aqueous extract of everlasting relative to the weight of the composition (%) | Weight % of essential oil of everlasting relative to the weight of the composition (%) | Weight % of aqueous extract of slender-beaded coral weed relative to the weight of the composition (%) |
|---|---|---|---|---|
| No. 1 | 0.01 | 0.5 | 0.1 | 3 |
| No. 2 | 0.02 | 0.01 | 0.05 | 1 |
| No. 3 | 0.01 | 0.2 | 0.01 | 2 |
| No. 4 | 0.03 | 0.1 | 0.1 | 0.5 |
| No. 5 | 0.1 | 0.01 | 0.05 | 3 |
| No. 6 | 0.03 | 0.1 | 0.05 | 2 |
| No. 7 | 0.01 | 0.01 | 0.2 | 0.1 |
| No. 8 | 0.02 | 0.02 | 0.1 | 1 |
| No. 9 | 0.03 | 0.01 | 0.05 | 2 |
| No. 10 | 0.1 | 0.1 | 0.1 | 3 |
| No. 11 | 0.05 | 0.05 | 0.02 | 0.5 |

Example 2: Effect on the Expression of Skin Genes of an Extract of Slender-Beaded Coral Weed, of Essential Oil of Everlasting and of a Mixture Including an Extract of Slender-Beaded Coral Weed and of Essential Oil of Everlasting For the extract of slender-beaded coral weed, it was a water-glycerol extract (50/50 v/v) of *Jania rubens* sold by the company CODIF under the commercial reference Actiporine 8G.

For the essential oil of everlasting, it was an essential oil obtained by hydrodistillation and provided by the companies TEPPE ROSSE, STEPHAN FRANCISCI, GAEC de l'ASTRATELLA or a mixture of two or three of these oils.

The transcriptome is all of the messenger RNAs derived from the expression of part of the genome in a given tissue or cell type. Characterization and quantification of the transcriptome make it possible to identify the genes regulated under particular conditions, to determine the mechanisms for regulating these genes and to define the expression networks or activation pathways of these genes. One of the techniques used to simultaneously measure the level of expression of a large number of different messenger RNAs is that of the DNA microarray. DNA microarrays make it possible to very rapidly measure and visualize the differences in expression on the scale of a whole genome.

1. Materials and Methods

The extract of slender-beaded coral weed, the essential oil of everlasting or the combination of the two extracts were placed in contact with skin explants maintained under survival conditions. The essential oil of everlasting was dissolved at 10% in dimethyl sulfoxide (DMSO) before being applied to the culture medium. The extract of slender-beaded coral weed was, for its part, diluted directly in the same culture medium.

4 skin explants originating from an abdominal plasty of a 62 year old patient were incubated independently. They were incubated in the presence of the extract of slender-beaded coral weed, of the essential oil of everlasting or of the combination thereof for 24 hours in a "skin culture medium" from the company Biopredic at 37° C. containing 5% $CO_2$ under a humid atmosphere (98%) at the air-liquid interface. 4 skin explants that were untreated or treated with the solvent DMSO at 1% were incubated under the same conditions.

Table 3 below summarizes the concentrations applied for each composition.

TABLE 3 concentration applied for each composition

| Composition | Percentage (%) |
|---|---|
| Extract of slender-beaded coral weed | 0.2 |
| Essential oil of everlasting | 0.1 |
| Extract of slender-beaded coral weed and essential oil of everlasting | 0.2 0.1 |

Extraction of the Total RNAs

After incubation, the skin explants were ground in the buffer recommended by the manufacturer of the RNeasy mini kit (Qiagen, Hilden, Germany) and the total RNAs were then extracted using this same kit. The total RNAs were quantified and their quality was then checked using the BIOanalyzer 2100 with the RNA 6000 Nano LabChip Kit (Agilent Technologies, Santa Clara, USA).

Measurement of the Gene Expression on an Oligonucleotide Microarray and Data Acquisition:

60 mer oligonucleotide microarrays on 1"×3" glass slides, SurePrint G3 Human Gene Expression 8×60 K v2 Microarray (G4851B, Agilent Technologies, Santa Clara, USA) were used for the analysis of the gene expression (SurePrint G3 Human Gene Expression 8×60 K v2, Agilent Technologies, Santa Clara, USA).

Documentation and the full experimental protocol are available on the Agilent Technologies website [32].

Briefly, reverse transcription and amplification of the total RNAs into cDNA and then into cRNA and labeling thereof with cyanine 3 are performed using the Low Input Quick Amp Labeling Kit (Agilent Technologies). Purification of the cRNAs was performed using the RNeasy mini kit (Qiagen, Hilden, Germany) and hybridization with the Microarray hybridization chamber kit (Agilent Technologies, Santa Clara, USA). The microarrays were then scanned using the SureScan scanner (Agilent Technologies, Santa Clara, USA) and the Scan control software (Agilent Technologies, Santa Clara, USA). The scanned images were then extracted and normalized with the Feature Extraction software (Agilent Technologies, Santa Clara, USA).

Statistical analysis of the data was performed using the GeneSpring GX 13 software (Agilent Technologies, Santa Clara, USA).

The Ingenuity Pathways Analysis software (Ingenuity® Pathway Analysis (IPA), Ingenuity Systems, Redwood City, Calif., USA—http://www.ingenuity.com) was then used to analyze and predict the state of activation of the biological pathways modulated with the extract of slender-beaded coral weed, the essential oil of everlasting or the combination thereof.

For each treatment condition, 4 independent labeling experiments were performed (i.e. 4 oligonucleotide microarrays per condition, corresponding to the 4 skin explants treated independently for each condition) to increase the data reproducibility.

The genes expressed by the treated skin explants were considered as being induced or inhibited if their level of differential expression was greater by a factor of 2 compared with those of the control explants. The untreated explants served as control for the condition treated with the extract of slender-beaded coral weed and the explants treated with the 1% DMSO solvent served as control for the condition treated with the essential oil of everlasting or the combination of the extract of slender-beaded coral weed and the essential oil of everlasting in combination. A moderated T-test corrected for the level of false positives was applied with the Benjamini & Hochberg procedure [33] by the GeneSpring software so as to calculate the statistical difference in gene expression between the untreated explants or the explants treated with the DMSO solvent and the explants treated with the active agents or the combination thereof. The genes whose p-value was less than or equal to 0.05 were considered as differentially expressed.

These genes were then analyzed with the Ingenuity Pathways Analysis software. This software allows functional analysis of the genes regulated under the various treatment conditions, analysis of the signaling pathways in which these genes are inscribed and analysis of the regulators upstream of these pathways. A Z-score was calculated by the software relative to the significantly regulated genes. A Z-score >2 or <−2 indicates within a 99% confidence interval that the induced or suppressed biological pathways are not induced or suppressed purely by chance, but quite specifically.

TABLE 4

Z-score of the pathway for the differentiation of epidermal cells in response to treatment of the skin explants with the extract of slender-beaded coral weed, the essential oil of everlasting and the combination thereof

| | Extract of slender-beaded coral weed | Everlasting essential oil (EO) | Extract of slender-beaded coral weed and everlasting EO |
|---|---|---|---|
| Differentiation of the epidermal cells | — | 1.948 | 2.398 |

The table below presents the difference in expression of the genes involved in the differentiation of the epidermal cells following treatment of the skin explants with the extract of slender-beaded coral weed, the essential oil of everlasting and the combination thereof.

TABLE 5 difference in expression as a function of incubation with an extract of slender-beaded coral weed, an essential oil of everlasting or a combination of extract of slender-beaded coral weed and an essential oil of everlasting

| GENES | | Genbank Accession | STATUS in the study: Expression relative to the untreated control or to the solvent control | | |
|---|---|---|---|---|---|
| Symbol | Name | | Slender-beaded coral weed | Everlasting EO | Slender-beaded coral weed and everlasting EO |
| AURKB | aurora kinase B | NM_004217 | — | −3.07 | −4.89 |
| CDK1 | cyclin-dependent kinase 1 | NM_001786 | — | −2.40 | −2.92 |
| EGF | epidermal growth factor | NM_001963 | — | — | 2.21 |
| FLG | Filaggrin | NM_002016 | — | — | 2.03 |
| FLG2 | Filaggrin family member 2 | NM_001014342 | — | — | 2.24 |
| FOXM1 | forkhead box M1 | NM_202002 | — | −2.75 | −2.79 |
| FOXN1 | forkhead box N1 | NM_003593 | — | — | −2.09 |
| GAK | cyclin G associated kinase | AK131464 | — | — | 2.35 |
| GLI2 | GLI family zinc finger 2 | NM_005270 | — | — | 2.04 |
| HDAC2 | histone deacetylase 2 | NM_001527 | — | 2.05 | 2.28 |
| HGF | hepatocyte growth factor (hepapoietin A; scatter factor) | NM_001010934 | — | — | 4.29 |
| HOXA7 | homeobox A7 | NM_006896 | — | — | −2.64 |
| IL20 | interleukin 20 | NM_018724 | — | 2.51 | 2.54 |
| LATS2 | large tumor suppressor kinase 2 | NM_014572 | — | — | 2.11 |
| MAPK8 | mitogen-activated protein kinase 8 | NM_001278547 | — | 2.45 | 2.68 |
| PPARD | peroxisome proliferator-activated receptor delta | NM_006238 | — | 2.85 | 3.06 |
| TNF | tumor necrosis factor | NM_000594 | — | — | −3.68 |
| TNFSF10 | tumor necrosis factor (ligand) superfamily, member 10 | NM_003810 | — | −8.80 | −12.02 |
| TNFSF12 | tumor necrosis factor (ligand) superfamily, member 12 | NM_003809 | — | −2.11 | −2.16 |
| TP63 | tumor protein p63 | NM_003722 | — | −3.03 | −3.39 |
| VDR | vitamin D (1,25-dihydroxyvitamin D3) receptor | NM_001017535 | — | −2.37 | −2.49 |
| WNT16 | wingless-type MMTV integration site family, member 16 | NM_057168 | — | −4.21 | −7.57 |

In the abovementioned table, the numerical value represents the stimulation or inhibition factor relative to untreated skin, db EST is a database collating the gene reference and also its sequence corresponding to the gene spotted on the 60 mer oligonucleotide microarrays on 1"∴3" glass slides, SurePrint G3 Human Gene Expression 8×60 K v2 Microarray (G4851B, Agilent Technologies, Santa Clara, USA), and "–" the absence of gene regulation.

The results obtained demonstrate that treatment of the explants by the combination of the extract of slender-beaded coral weed and of the essential oil of everlasting induces an increase in the differentiation of the epidermal cells with a Z-score of 2.398 whereas the essential oil of everlasting alone only induces a Z-score of 1.948, which is insignificant, and that the extract of slender-beaded coral weed alone does not induce this pathway.

Thus, as demonstrated above, an example of a composition according to some embodiments including a mixture of at least one extract of slender-beaded coral weed and of essential oil of everlasting advantageously makes it possible, especially by increasing the differentiation of the epidermal cells, to reinforce the barrier function of the skin, to maintain better moisturization, to stimulate the skin's defenses and to enhance or improve the surface quality of the skin.

As demonstrated in the table, the mixture including the extract of slender-beaded coral weed and the essential oil of everlasting advantageously makes it possible to stimulate the expression of the genes coding for filaggrin and for filaggrin 2. These two proteins play a fundamental role in maintaining the skin moisturization. They are co-located in the keratohyalin granules of the granulous keratinocytes and in the cytoplasmic matrix of the corneocytes. When filaggrin is degraded to amino acids, it partly constitutes the skin's natural moisturizing factor (NMF) [21]. The exact role of filaggrin 2 has not yet been discovered, but it appears to be similar to that of filaggrin and is of importance for the correct functioning of cornification and for the constitution of a functional stratum corneum [34].

The mixture including the extract of slender-beaded coral weed and the essential oil of everlasting also advantageously makes it possible to inhibit expression of the gene coding for HOXA7. Overexpression of this gene is known to reduce the induction of transglutaminase 1 and expression of HOXA7 is inversely correlated to keratinocyte differentiation which is involved in the correct functioning and the formation of the epidermal barrier [35].

Furthermore, the mixture including the extract of slender-beaded coral weed and the essential oil of everlasting also advantageously makes it possible to induce the gene coding for cyclin G associated kinase (GAK) which is known to be involved in the formation of the epidermal barrier. Specifically, mice in which the GAK gene has been specifically deleted in the skin die at birth by desiccation because their epidermal barrier is defective [36] due to a defect in the differentiation process such that the absence of multiple layers which normally form the epidermis and the stratum corneum does not develop correctly.

Similarly, inhibition of the gene coding for tumor necrosis factor alpha (TNF-α) by the mixture of the aqueous extract and of the essential oil of everlasting leads to a barrier function that is advantageously reinforced by the mixture of these two active agents. Specifically, the proteins filaggrin and loricrin are known to be inhibited by TNF-α. The mixture of the extract of slender-beaded coral weed and of essential oil of everlasting, by advantageously inhibiting TNF-α, allows the expression of loricrin and filaggrin and thus reinforcement of the epidermal barrier.

Moreover, the epidermal growth factor (EGF) and hepatocytic growth factor (HGF) are induced only in the presence of the mixture of the extract of slender-beaded coral weed and of the essential oil of everlasting. These growth factors are essential for keratinocyte proliferation and their induction increases epidermal turnover. Decreasing the proliferative capacity of keratinocytes participates in the thinning of the epidermis in the course of aging. Thus, treatment with the mixture of the two extracts synergistically restores this thickness [37]. The other genes also regulated by the mixture of the extract of slender-beaded coral weed and of the essential oil of everlasting (table 5) also contribute toward the formation of the epidermal barrier or epidermal turnover.

This example clearly demonstrates by ex vivo transcriptome analysis with DNA microarrays that the composition of some embodiments makes it possible to stimulate genes involved in particular in the differentiation of the epidermal cells.

This example also clearly demonstrates that a composition including an extract of slender-beaded coral weed and an extract of everlasting advantageously makes it possible to stimulate the epidermal barrier functioning and/or function, making it possible in particular to protect the skin against external attack, to maintain/increase skin moisturization, to prevent and/or treat aging of the skin, for example by conserving and/or restoring the thickness of the epidermis, to enhance or improve the surface quality of the skin and thus to have a complexion that is more radiant due to better light reflection.

Example 3: Test of Use of an Example of a Cosmetic Composition According to Some Embodiments and Evaluation of the Cosmetic Qualities of the Composition In order to validate the effects of an example of a composition according to some embodiments, a use test was performed on an independent panel of female volunteers.

The use test was conducted on a panel of 54 volunteers between 42 and 65 years old (average age of 56), presenting with wrinkles and fine lines, a lack of radiance and a lack of skin firmness on the skin of the face and neck.

After breathing in the fragrance, the composition was applied twice a day morning and evening for 28 days in a small dose using a spatula, by a smoothing movement from the interior to the exterior of the face and neck, which were cleansed beforehand.

The composition used included the compounds indicated in table 1 and 0.03% by weight of oily extract of everlasting, 0.1% by weight of aqueous extract of everlasting, 0.05% by weight of essential oil of everlasting and 2% by weight of aqueous extract of slender-beaded coral weed relative to the total weight of the composition.

TABLE 6 overall judgment of the composition
General assessment of the product

| On application | |
|---|---|
| The texture is silky | 93% |
| The texture changes in the course of application | 76% |
| The product melts on the skin | 78% |
| Immediately after the first application | |
| The skin is nourished | 94% |
| The skin is comforted | 93% |
| The skin is supple | 91% |
| The skin appears uncreased | 70% |
| The skin is more tonic | 70% |
| After 28 days of use | |
| The skin is intensely nourished | 83% |
| The product offers a real sensation of comfort | 83% |
| The skin is more supple | 81% |
| The lines appear redefined | 78% |
| The skin is firmer | 61% |
| The skin is more elastic | 69% |

As demonstrated in table 6, an example of a composition according to some embodiments including 0.03% by weight of oily extract of everlasting, 0.1% by weight of aqueous extract of everlasting, 0.05% by weight of essential oil of everlasting and 2% by weight of aqueous extract of slender-beaded coral weed relative to the total weight of the composition was thus considered as effective. In particular, as demonstrated, an example of a composition according to some embodiments makes it possible to treat the signs of aging, especially an enhancement or improvement in skin moisturization, the treatment of wrinkles and fine lines, the enhancement or improvement in the elasticity and firmness of the skin. As demonstrated, the composition advantageously allows treatment immediately after application and over time.

Example 4: Test of Use of an Example of a Cosmetic Composition According to Some Embodiments and Evaluation of the Cosmetic Qualities of the Composition The use test was conducted on a panel of 35 female asiatic volunteers between 40 and 65 years old (54.6 years old on average) representing all skin types, for example dry, normal, combination and greasy skin. They had dull skin, a light complexion with the presence of pigmentation marks, namely with a density defined according to the Aging Atlas of grade≥2, and at least one well-defined mark on the cheek, for example from 2.5 to 3 mm in diameter.

After breathing in the fragrance, the composition was applied twice daily morning and evening for up to 12 weeks in a small dose using a spatula, by a smoothing movement from the interior to the exterior of the face and of the neck, which were cleansed beforehand.

The composition used included the compounds indicated in table 1 and 0.03% by weight of oily extract of everlasting, 0.1% by weight of aqueous extract of everlasting, 0.08% by weight of essential oil of everlasting and 2% by weight of aqueous extract of slender-beaded coral weed relative to the total weight of the composition.

TABLE 7

| overall judgment of the composition | |
|---|---|
| Immediately after the first application | |
| The complexion is illuminated | 80% |
| The skin is radiant | 89% |
| The skin is supple | 94% |
| After 8 weeks of use | |
| The complexion is visibly lightened | 94% |
| The skin appears luminous | 91% |
| The appearance of pigmentation irregularities, such as blackheads, is reduced | 86% |
| The size of the pigmentation defects is reduced | 89% |
| The complexion is unified | 86% |
| The product reduces the appearance of differences in complexion | 77% |
| The skin is freed of its dull veil | 83% |
| The capacities of the skin to capture and reflect light are increased | 83% |
| The skin reveals its clarity | 80% |
| The skin regains its natural translucency | 94% |
| The skin regains its original light | 94% |
| The skin is smoother | 100% |
| The skin texture appears refined | 100% |
| The irregularities of the skin texture are reduced | 89% |
| The skin quality is enhanced or improved | 97% |
| The skin uniformity is enhanced or improved | 100% |
| The skin appears fairer | 94% |
| The skin shines with youthful radiance | 83% |
| The skin appears serene | 86% |
| The face is illuminated | 94% |
| The skin appears more beautiful | 94% |
| After 12 weeks of use | |
| The complexion is visibly lightened | 91% |
| The appearance of pigmentation irregularities, such as blackheads, is reduced | 80% |
| The size of the pigmentation defects is reduced | 89% |
| The complexion is unified | 80% |
| The capacities of the skin to capture and reflect light are increased | 91% |
| The skin reveals its clarity | 89% |
| The skin regains its natural translucency | 94% |
| The skin regains its original light | 91% |
| The skin texture appears refined | 94% |
| The irregularities of the skin texture are reduced | 94% |
| The skin quality is enhanced or improved | 94% |
| The skin appears lighter | 91% |
| The skin shines with youthful radiance | 89% |
| The complexion is harmonious | 89% |

TABLE 7-continued

| overall judgment of the composition | |
|---|---|
| The skin appears free of defects | 69% |
| The complexion is visibly lightened | 89% |
| The skin appears more beautiful | 91% |

As demonstrated in table 7, an example of a composition according to some embodiments including 0.03% by weight of oily extract of everlasting, 0.1% by weight of aqueous extract of everlasting, 0.08% by weight of essential oil of everlasting and 2% by weight of aqueous extract of slender-beaded coral weed relative to the total weight of the composition was thus considered as efficient. In particular, as demonstrated, an example of a composition according to some embodiments makes it possible to treat the signs of aging of asiatic skin, especially an enhancement or improvement of the radiance of the complexion, of its homogeneity, of its luminosity, and/or to reduce the skin pigmentation defects. In addition, as demonstrated, an example of a composition according to some embodiments makes it possible to enhance or improve the appearance of the skin, in particular with a more uniform and smoother texture. As demonstrated, the composition advantageously allows treatment immediately after application and over time.

In addition, a visual study of the density of the pigmentation marks and of the radiance of the complexion using the C.L.B.T. score as described in Musnier et al. Visual evaluation in vivo of 'complexion radiance' using the C.L.B.T. sensory methodology. Skin Res Technol. 2004 February; 10(1):50-6 [38] was performed. Each parameter was measured after 2 and 3 months of application of the composition and compared with the measurements taken before the first application of the composition. Thus, an evaluation of the facial skin of the 35 abovementioned volunteers was performed by three trained judges.

The color descriptors, namely Olive, Yellow or Pink, and the physical appearance descriptors, namely the luminosity, brightness and transparency, were defined beforehand. In particular, an increase in the pink color indicated a healthier appearance effect, a decrease in the "yellow" color indicated a good effect (less yellowish complexion), a decrease in the "olive" color indicated a good effect and a healthier appearance effect (the complexion is less olive-greenish), an increase in the luminosity: the skin reflects light slightly more intensely, an increase in the luminosity: the complexion has an appearance in terms of texture and color, an increase in transparency: the skin is thinner.

The evaluation was performed in a black room with a controlled temperature and atmosphere (22±2° C., 50±10% hygrometry). After 20 minutes of acclimatization in the controlled room, the individuals were placed between two lamps diffusing "daylight".

The complexion was evaluated individually by three trained judges, without knowledge of the data obtained in the preceding stage. The three judges were not permitted to communicate with each other. Evaluation of the three colors was performed using a visual scale of the three main colors of facial skin (olive/yellow/pink). A score was attributed for each color representing a percentage of saturation. Each judge attributed a score for each color at T0, i.e. before treatment.

A Clinical evaluation of the luminosity, brightness and transparency (LBT) was performed by three trained judges. This evaluation was retranscribed on an analog scale extending from 0 (no luminosity/brightness/transparency) to 100 (maximum luminosity/brightness/transparency).

The mean of the scores attributed by the three judges was determined for each of the descriptors.

For the color descriptors, the results were expressed as a percentage of saturation of the color.

For the LBT descriptors, the results were retranscribed by a score ranging from 0 to 10.

Interpretation of the C.L.B.T. results was performed on the basis of the significant variations in the descriptors taken separately:

Statistical analysis of the data: the distribution normality was checked by the Shapiro-Wilk test (1% threshold). Statistical analysis of the change in the measured parameters was performed by the paired bilateral Student t test (in the case of a normal distribution) or of the Wilcoxon test (non-normal distribution). The significance threshold was set at 5%.

Table 8 below summarizes the results obtained:

| Parameters | After 2 months | After 3 months |
|---|---|---|
| Density of marks | −23% | −19% |
| Uniformity of complexion | +17% | +16% |
| CLBT score | | |
| Olive color | Ns | Ns |
| Yellow color | −3.9% | −6% |
| Pink color | Ns | Ns |
| Luminosity | Ns | Ns |
| Clarity | +3.7 | +6.1 |
| Transparency | Ns | Ns |

As demonstrated in table 8 below, an example of a composition according to some embodiments advantageously makes it possible to reduce the density of pigmentation marks and enhances or improves the uniformity of the complexion. The composition also lightens the complexion (+6.1% at 3 months) and reduces its yellow shade (−6% at 3 months). This example thus clearly demonstrates that an example of a composition according to some embodiments is useful and efficient in a cosmetic treatment of aging of the skin.

As demonstrated in this example, the compositions according to some embodiments are effective with various skin phototypes, for example asiatic phototypes.

REFERENCES

1. Koblenzer C S. Psychologic aspects of aging and the skin. Clinics Dermatol 1996; 14:171-7
2. West M D. The cellular and molecular biology of skin aging. Arch dermatol 1994; 130:87-95
3. Grove G L, Kligman A M. Age-associated changes in human epidermal cell renewal. J Gerontol 1983; 38:137-42
4. Watt F M. Involucrin and other markers of keratinocyte terminal differentiation. J Invest Dermatol. 1983; 81:100s-3s
5. Mehrel T, Hohl D, Rothnagel J A, Longley M A, Bundman D, Cheng C, Lichti U, Bisher M E, Steven A C, Steinert P M, et al. Identification of a major keratinocyte cell envelope protein, loricrin. Cell. 1990; 61:1103-12
6. Candi E, Schmidt R, Melino G. The cornified envelope: a model of cell death in the skin. Nat Rev Mol Cell Biol. 2005; 6:328-40
7. Watt F M, Green H. Involucrin synthesis is correlated with cell size in human epidermal cultures. J. Cell Biol. 1981; 90:738-742.
8. Ruhrberg C, Hajibagheri M A, Parry D A, Watt F M. Periplakin, a novel component of cornified envelopes and desmosomes that belongs to the plakin family and forms complexes with envoplakin. J. Cell Biol. 1997; 139:1835-1849.
9. Ruhrberg C, Hajibagheri M A, Simon M, Dooley T P, Watt F M. Envoplakin, a novel precursor of the cornified envelope that has homology to desmoplakin. J. Cell Biol. 1996; 134:715-729.
10. DiColandrea T, Karashima T, Maatta A, Watt F M. Subcellular distribution of envoplakin and periplakin: insights into their role as precursors of the epidermal cornified envelope. J. Cell Biol. 2000; 151:573-586.
11. Sevilla L M, Nachat R, Groot K R, Klement J F, Uitto J, Djian P, Maatta A, Watt F M., Mice deficient in involucrin, envoplakin, and periplakin have a defective epidermal barrier. J. Cell Biol. 2007; 179:1599-1612.
12. Kalinin A, Marekov L N, Steinert P M. Assembly of the epidermal cornified cell envelope. J. Cell Sci. 2001; 114:3069-3070.
13. Eckert R L, Sturniolo M T, Broome A M, Ruse M, Rorke E A. Transglutaminase function in epidermis. J. Invest. Dermatol. 2005; 124:481-492.
14. Steinert P M, Marekov L N. Initiation of assembly of the cell envelope barrier structure of stratified squamous epithelia. Mol. Biol. Cell 1999; 10:4247-4261.
15. Ahvazi B, Boeshans K M, Idler W, Baxa U, Steinert P M. Roles of calcium ions in the activation and activity of the transglutaminase 3 enzyme. J. Biol. Chem. 2003; 278: 23834-23841.
16. Jackson B, Tilli C M, Hardman M J, Avilion A A, MacLeod M C, Ashcroft G S, Byrne C. Late cornified envelope family in differentiating epithelia—response to calcium and ultraviolet irradiation. J. Invest. Dermatol. 2005; 124:1062-1070.
17. Marshall D, Hardman M J, Nield K M, Byrne C. Differentially expressed late constituents of the epidermal cornified envelope. Proc. Natl. Acad. Sci. U.S.A. 2001; 98:13031-13036.
18. Denda M, Tomitaka A, Akamatsu H, Matsunaga K. Altered distribution of calcium in facial epidermis of aged adults. J. Invest. Dermatol. 2003; 121:1557-1558.
19. Chavanas S, Méchin M C, Nachat R, Adoue V, Coudane F, Serre G, Simon M. Peptidylarginine deiminases and deimination in biology and pathology: relevance to skin homeostasis. J Dermatol Sci. 2006; 44:63-72.
20. Denecker G, Ovaere P, Vandenabeele P, Declercq W. Caspase-14 reveals its secrets. J Cell Biol. 2008; 180:451-8.
21. Brown S J, McLean W H. One remarkable molecule: filaggrin. J Invest Dermatol. 2012; 132:751-62.
22. Steinert P M, Cantieri J S, Teller D C, Lonsdale-Eccles J D, Dale B A. Characterization of a class of cationic proteins that specifically interact with intermediate filaments. Proc Natl Acad Sci USA. 1981 July; 78(7):4097-101.
23. Rawlings A V, Harding C R. Moisturization and skin barrier function. Dermatol Ther. 2004; 17 Suppl 1:43-8.
24. Elias P M, Steinhoff M. "Outside-to-inside" (and now back to "outside") pathogenic mechanisms in atopic dermatitis. J Invest Dermatol. 2008 May; 128(5):1067-70.
25. FR3000389
26. FR0111224
27. FR0605953
28. FR0905904
29. FR1153960
30. Farid Chemat: Eco-extraction du végétal, Editions Dunod, 2011.

31. BENAISSI, K. Le CO2 supercritique appliqué à l'extraction végétale. Techniques de l'ingénieur Développement de solvants alternatifs et intensification des procédés. 2013. http://www.techniques-ingenieur.fr/

32. http://www.chem.agilent.com/library/usermanuals/Public/G4140-90040_GeneExpression_OneColor_6.6.pdf 33. Bejamini Y & Hochberg Y. Controlling the false discovery rate: a practical and powerful approach to multiple testing. Journal of the Royal Statistical Society B. 1995; 57:289-300.

34. Wu Z, Hansmann B, Meyer-Hoffert U, Gläser R, Schröder J M. Molecular identification and expression analysis of filaggrin-2, a member of the S100 fused-type protein family. PLoS One. 2009; 4:e5227

35. La Celle P T, Polakowska R R. Human homeobox HOXA7 regulates keratinocyte transglutaminase type 1 and inhibits differentiation. J Biol Chem. 2001; 276:32844-53

36. Segre J A, Bauer C, Fuchs E. Klf4 is a transcription factor required for establishing the barrier function of the skin. Nat Genet. 1999; 22:356-60

37. Sato C, Tsuboi R, Shi C M, Rubin J S, Ogawa H. Comparative study of hepatocyte growth factor/scatter factor and keratinocyte growth factor effects on human keratinocytes. J Invest Dermatol. 1995; 104:958-63

38. Musnier C, Piquemal P, Beau P, Pittet J C. Visual evaluation in vivo of 'complexion radiance' using the C.L.B.T. sensory methodology. Skin Res Technol. 2004 February; 10(1):50-6.

The invention claimed is:

1. A cosmetic composition, comprising:
   at least one extract of slender-beaded coral weed,
   an essential oil of everlasting, and
   at least one aqueous extract of everlasting and/or an oily extract of everlasting, wherein the concentration of extract of slender-beaded coral weed is from 0.001% to 5% by weight relative to the total weight of the composition.

2. The composition as claimed in claim 1, wherein the extract of slender-beaded coral weed is chosen from the group comprising a water-soluble extract of slender-beaded coral weed, a liposoluble extract of slender-beaded coral weed or a mixture thereof.

3. The composition as claimed in claim 2, wherein the concentration of extract of everlasting is from 0.001% to 10% by weight relative to the total weight of the composition.

4. The composition as claimed in claim 2, wherein the extract of everlasting is an extract of *Helichrysum italicum*.

5. The composition as claimed in claim 1, wherein the concentration of extract of everlasting is from 0.001% to 10% by weight relative to the total weight of the composition.

6. The composition as claimed in claim 1, wherein the extract of everlasting is an extract of *Helichrysum italicum*.

7. The composition as claimed in claim 1, wherein the extract of slender-beaded coral weed is an extract of *Jania rubens*.

8. The composition as claimed in claim 1, wherein the composition is in a form chosen from a cream, a serum, a milk, a gel, a lotion, an ointment, an oil, a balm and a mask.

9. A method of using the composition as claimed in claim 1 for nontherapeutic antiaging cosmetic treatment, comprising:
   applying the composition to skin.

10. A method of using the composition as claimed in claim 1 for nontherapeutic cosmetic treatment, comprising:
    applying the composition to skin for treating aging of the skin, wrinkles and fine lines, loss of skin firmness, loss of skin elasticity and dry skin.

11. A method of using the composition as claimed in claim 1 for nontherapeutic cosmetic treatment, comprising:
    applying at least one extract of slender-beaded coral weed and at least one extract of everlasting to skin for protecting the skin against external attack.

12. A method of using the composition as claimed in claim 1, comprising:
    applying at least one extract of slender-beaded coral weed and at least one extract of everlasting to skin in a nontherapeutic cosmetic treatment of aging of the skin, wrinkles and fine lines, loss of firmness, loss of elasticity and/or dry skin.

13. A method of using the composition as claimed in claim 1 for a nontherapeutic cosmetic treatment, comprising:
    applying the composition to the skin for protecting the skin against external attack.

14. A nontherapeutic cosmetic treatment process, comprising:
    applying the cosmetic composition as claimed in claim 1 to skin.

15. A cosmetic care kit for using the composition of claim 1 in a nontherapeutic cosmetic treatment for protecting skin against external attack, the kit comprising:
    the composition of claim 1, and
    a notice for use.

* * * * *